US00PP30672P2

(12) United States Plant Patent
Klemm et al.

(10) Patent No.: US PP30,672 P2
(45) Date of Patent: Jul. 9, 2019

(54) ***DIANTHUS* PLANT NAMED 'KLEDG18274'**

(50) Latin Name: ***Dianthus* sp.**
Varietal Denomination: KLEDG18274

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,359

(22) Filed: Aug. 7, 2018

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./263.1, 272, 273
See application file for complete search history.

*Primary Examiner* — Susan McCormick Ewoldt
*Assistant Examiner* — Karen M Redden
(74) *Attorney, Agent, or Firm* — Bethany Reid Roahrig; Cochran Freund & Young LLC

(57) ABSTRACT

A new *Dianthus* plant particularly distinguished by red purple flowers with a dark purple pattern, very early flowering, and an upright habit, is disclosed.

1 Drawing Sheet

Genus and species: *Dianthus* sp.
Variety denomination: 'KLEDG18274'.

CROSS REFERENCE TO RELATED APPLICATIONS

A Canadian Plant Breeders Rights Application for this variety was filed on Apr. 27, 2018, Application No. 18-9431, and a European Community Plant Variety Protection Application for this variety was filed on Apr. 24, 2018, Application No. 2018/1128. 'KLEDG18274' has not been sold or made publicly available more than one year prior to the filing date of the present application.

BACKGROUND OF THE NEW PLANT

The present invention comprises a new and distinct variety of *Dianthus*, botanically known as *Dianthus caryophyllus*, and hereinafter referred to by the variety name 'KLEDG18274'. 'KLEDG18274' originated from an open pollination of the proprietary female parent 'DSS-2011-0087' (unpatented) and an unknown male *Dianthus* variety in June 2013, in Stuttgart, Germany. A single plant was selected in July 2014 and designated 'KLEDG18274'.

In September 2014, 'KLEDG18274' was first vegetatively propagated by vegetative cuttings in Stuttgart Germany. 'KLEDG18274' was found to reproduce true to type in successive generations of asexual propagation in Latina, Italy via vegetative stem cuttings.

SUMMARY

The following are the most outstanding and distinguishing characteristics of this new variety when grown under normal horticultural practices in Stuttgart, Germany.

1. Red purple flowers with a dark purple pattern;
2. Very early flowering; and
3. An upright habit.

DESCRIPTION OF THE PHOTOGRAPH

This new *Dianthus* plant is illustrated by the accompanying photograph of a plant approximately 10 weeks old and grown in a greenhouse in Stuttgart, Germany. The photograph shows the whole plant, including the flowers and foliage and buds and was taken in March 2017 in Stuttgart, Germany.

The colors shown are as true as can be reasonably obtained by conventional photographic procedures.

DESCRIPTION OF THE NEW VARIETY

The following detailed descriptions set forth the distinctive characteristics of 'KLEDG18274'. The data which define these characteristics were collected from asexual reproductions carried out in Stuttgart, Germany. Data was collected in April 2018 on 6-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* sp.
- *Common*.—Pot carnation.
- *Designation*.—'KLEDG18274'.

Parentage:
- *Female parent*.—The proprietary *Dianthus* variety 'DSS-2011-0087' (unpatented).
- *Male parent*.—An unknown proprietary *Dianthus* variety.

Plant:
- *Plant form*.—Upright.
- *Plant height*.—12.0 cm to 14.0 cm.
- *Plant diameter or spread*.—16.0 cm to 18.0 cm.
- *Propagation type*.—Vegetative cuttings, stem cutting.
- *Time to produce a rooted young plant*.—10 to 14 days.

*Root description*.—White, fine.
*Rooting habit* (*shape*).—Lanceolate.

Lateral branches:
*Number of lateral branches*.—5 to 8.
*Strength*.—Moderate to strong.
*Length*.—10.0 cm to 12.0 cm.
*Diameter*.—0.3 cm to 0.6 cm.
*Internode length*.—2.0 cm to 2.5 cm.
*Number of internodes per branch/stem*.—4 to 6.
*Node length*.—0.3 cm to 0.4 cm.
*Node diameter*.—0.3 cm.
*Texture*.—Smooth.
*Color*.—RHS 136B.
*Branch/stem appearance*.—Solid.

Foliage:
*Arrangement*.—Opposite.
*Length*.—4.0 cm to 6.0 cm.
*Width*.—0.4 cm to 0.6 cm.
*Shape*.—Lanceolate.
*Apex*.—Acute.
*Base*.—Obtuse.
*Margin*.—Entire.
*Texture* (*both upper and lower surfaces*).—Smooth.
*Immature leaf color*.—Upper surface: RHS 143A. Lower surface: RHS 138A.
*Mature leaf color*.—Upper surface: RHS 139A. Lower surface: RHS N138A.
*Venation pattern*.—Parallel.
*Venation color*.—Upper surface: RHS 139A. Lower surface: RHS N138A.

Flowers:
*Flower type and habit*.—Single, double petal rings, small sprays.
*Fragrance*.—Present, typical of carnations.
*Natural flowering season*.—Spring to fall.
*Position of flowers relative to the foliage*.—Moderately above.
*Number of flowers per spray*.—4 to 6.
*Flower longevity on the plant*.—14 to 17 days.
*Buds*.—Length: 1.0 cm to 1.2 cm. Diameter: 0.4 cm to 0.6 cm. Shape: Elliptic. Color: RHS 145A (at the base), RHS 146A (in the middle), and RHS 187A (at the tip). Extrusion of the styles at the bud stage: Absent.
*Corolla*.—Quantity of petals and arrangement: 8 to 10 in two whorls. Corolla height: 0.3 cm to 0.5 cm. Corolla diameter: 2.0 cm to 2.6 cm. Petal length: 2.5 cm to 3.0 cm. Petal width: 1.2 cm to 1.5 cm. Petal shape: Spoon-shaped. Petal apex: Obtuse. Petal base: Acute. Petal margin: Crenate. Depth of petal margin: Shallow. Petal texture (both upper and lower surfaces): Smooth. Petal luster (both surfaces): Dull. Petal color: Immature: Upper surface: RHS 67A (outer ring) and RHS 59A (inner ring). Lower surface: RHS 73A. Mature: Upper surface: RHS N74A (outer ring) and RHS 59B (inner ring). Lower surface: RHS N74C.
*Calyx*.—Quantity of sepals and arrangement: Composed of 5 sepals, fused. Shape: Campanulate. Calyx height: 0.5 cm to 1.2 cm. Calyx diameter (at the apex): 0.4 cm to 0.6 cm. Sepal texture (both upper and lower surfaces): Smooth. Sepal color: Upper surface: RHS 137A (in the middle, at the base and tip) and RHS 142C (at the side). Lower surface: RHS 137D (in the middle, at the base to tip) and RHS 142C (at the side). Sepal length: 0.7 cm to 0.9 cm. Sepal diameter: 0.5 cm to 0.8 cm. Sepal apex: Acute. Sepal base: Obtuse. Sepal margin: Entire. Sepal luster (both surfaces): Dull. Sepal arrangement: Fused.

Peduncles:
*Length*.—1.0 cm to 1.5 cm (last internode); whole stem 10.0 cm to 12.0 cm.
*Diameter*.—0.1 cm to 0.2 cm.
*Strength*.—Moderate.
*Texture*.—Smooth.
*Color*.—RHS N138A.

Reproductive organs:
*Stamens*.—Quantity per flower: 3 to 5. Filament length: 0.5 cm. Filament color: RHS 157D. Anther length: 0.1 cm. Anther diameter: 0.05 cm. Anther color: RHS 73C. Pollen amount: Very sparse.
*Pistils*.—Quantity per flower: 1. Pistil length: 1.8 cm to 2.0 cm. Style length: 1.0 cm to 1.4 cm. Style color: RHS N155D. Stigma shape: Filamentous. Stigma color: RHS 72B. Ovary size: 0.6 cm to 0.8 cm. Ovary shape: Oval. Ovary color: RHS 145C.

Fruit and seed set: Seed is sometimes observed, but no information on the seed is available.

Disease and pest/insect resistance: No disease and pest/insect resistance observed.

COMPARISON WITH PARENTAL LINE AND KNOWN VARIETY

'KLEDG18274' is distinguished from its female parent as described in Table 1.

TABLE 1

Comparison with Parental Lines

| Characteristic | 'KLEDG18274' | Female Parent 'DSS-2011-0087' |
|---|---|---|
| Earliness | Very early | Medium early |
| Color pattern | Red purple with a dark purple | Dark red with a dark red pattern |

'KLEDG18274' can be compared to the commercial *Dianthus* variety 'Pink Kisses', also known as 'KLEDG12163' (U.S. Plant Pat. No. 24,707). Differences between the varieties are described in Table 2.

TABLE 2

Comparison with Similar Variety

| Characteristic | 'KLEDG18274' | 'Pink Kisses' |
|---|---|---|
| Earliness | Very early | Medium late (4 to 6 weeks later) |

We claim:

1. A new and distinct variety of *Dianthus* plant designated 'KLEDG18274' as illustrated and described herein.

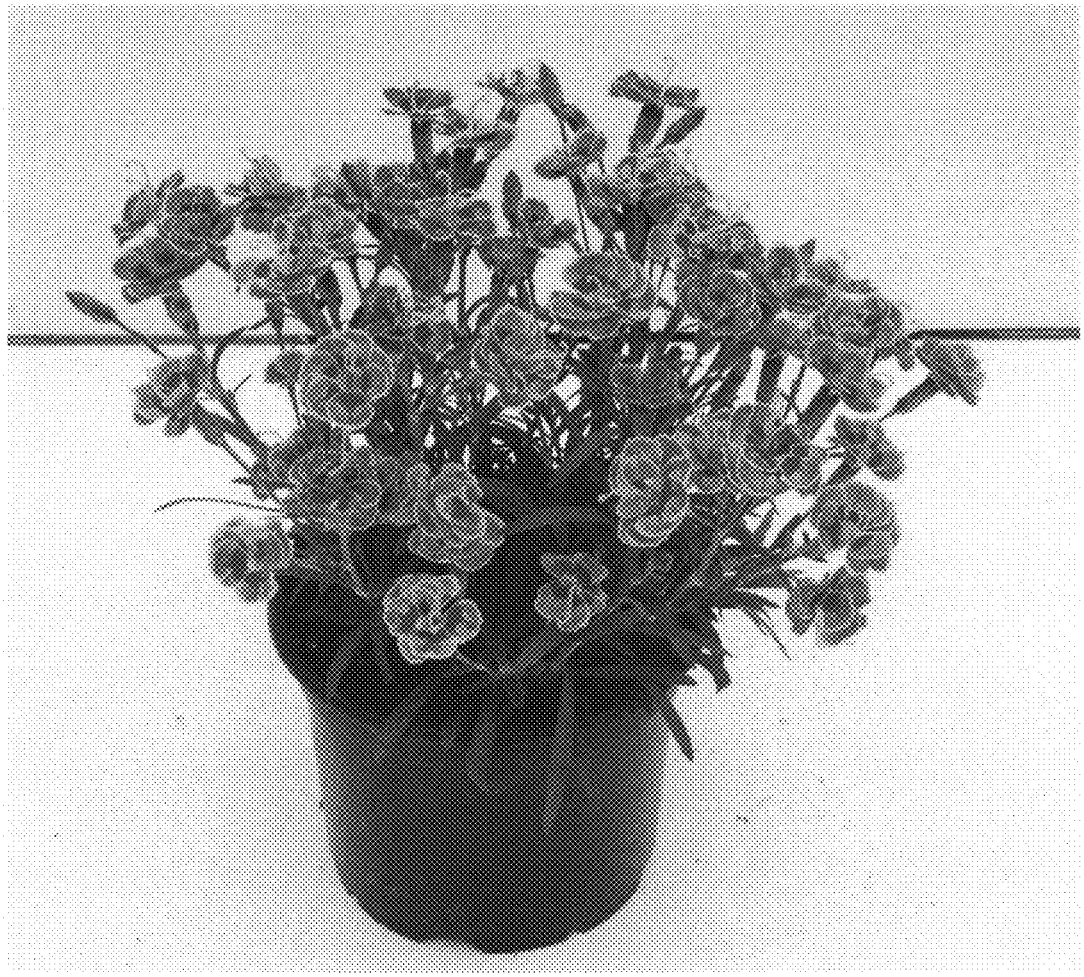

* * * * *